US005756706A

United States Patent [19]
Mansour et al.

[11] Patent Number: 5,756,706
[45] Date of Patent: May 26, 1998

[54] PROCESSES FOR THE DIASTEREOSELECTIVE SYNTHESIS OF NUCLEOSIDE ANALOGUES

[75] Inventors: Tarek Mansour, Montreal; Allan H. L. Tse, St. Laurent, both of Canada

[73] Assignee: BioChem Pharma Inc., Laval, Canada

[21] Appl. No.: 142,389

[22] PCT Filed: May 20, 1992

[86] PCT No.: PCT/CA92/00209

§ 371 Date: May 13, 1994

§ 102(e) Date: May 13, 1994

[87] PCT Pub. No.: WO92/20696

PCT Pub. Date: Nov. 26, 1992

Related U.S. Application Data

[63] Continuation-in-part of Ser. No. 703,379, May 21, 1991, abandoned.

[51] Int. Cl.$^6$ .................................................. C07H 19/24
[52] U.S. Cl. .......................... 536/27.11; 536/4.1; 549/63
[58] Field of Search ......................... 536/27.11; 549/63

[56] References Cited

U.S. PATENT DOCUMENTS

| 4,231,945 | 11/1980 | McCombie | 536/17 |
|---|---|---|---|
| 4,383,114 | 5/1983 | Vince | 544/277 |
| 4,882,316 | 11/1989 | Lambert et al. | 514/28.2 |
| 5,204,466 | 4/1993 | Liotta et al. | 544/317 |
| 5,210,085 | 5/1993 | Liotta et al. | 514/274 |

FOREIGN PATENT DOCUMENTS

| 0 071 926 A | 2/1983 | European Pat. Off. . |
|---|---|---|
| 0 266 042 A | 5/1988 | European Pat. Off. . |
| 0 337 713 A | 10/1989 | European Pat. Off. . |
| 0 349 242 A | 3/1990 | European Pat. Off. . |
| 0 363 582 A | 4/1990 | European Pat. Off. . |
| 0 382 526 A | 8/1990 | European Pat. Off. . |
| 1445013 | 5/1966 | France . |
| WO 89/04662 | 6/1989 | WIPO . |
| WO 90/01492 | 2/1990 | WIPO . |
| WO 90/12023 | 10/1990 | WIPO . |
| WO 91/01326 | 2/1991 | WIPO . |
| 9111186 | 8/1991 | WIPO . |
| WO 91/11186 | 8/1991 | WIPO . |
| WO 91/17159 | 11/1991 | WIPO . |
| WO 92/10496 | 6/1992 | WIPO . |
| WO 92/14743 | 9/1992 | WIPO . |
| WO 92/18517 | 10/1992 | WIPO . |

OTHER PUBLICATIONS

Lukevics et al., *Nucleosides Synthesis—Organosilicon Methods*, Ellis Norwood, New York, NY, 1991.

Tann et al., "Fluorocarbohydrates in Synthesis. An Efficient Synthesis of 1-(2-Deoxy-2-fluoro-β-D-arabinofuranosyl)5-iodouracil (β-FIAU) and 1-(2-Deoxy-2-fluoro-β-D-arabinofuranosyl)thymine (β-FMAU)," *J. Organic Chem.*, 50(19), 3644–3647 (Sep. 20, 1985).

Brodfuehrer et al., "A Stereocontrolled Synthesis of 1,3,5-Tri-O-benzoyl-α-D-ribofuranose," *J. Organic Chem.*, 50(14), 2597–2598 (Jul. 12, 1985).

Goodman, "Chemical Syntheses and Transformations of Nucleosides," in *Basic Principles in Nucleic Acid Chemistry*, vol. 1, Academic Press, New York, 1974, pp. 106–110.

March, *Advanced Organic Chemistry*, McGraw–Hill Book Co., New York, 1968, pp. 896–897.

M. Fieser, *Reagents for Organic Synthesis*, vol. 8, Wiley–Interscience, New York, 1980, pp. 261–263.

M. Fieser, *Reagents for Organic Synthesis*, vol. 12, Wiley–Interscience, New York, 1986, pp. 543–547.

Aggarwal et al. "Synthesis and Biological Evaluation of Prodrugs of Zidovudine", *J. Med. Chem.*, vol. 33, pp. 1505–1510 (1990).

Beres et al., "Stereospecific Synthesis And Antiviral Properties of Different Enantiomerically Pure Carbocyclic 2'-Deoxyribonucleoside Analogues Derived From Common Chiral Pools: (+)-(1R,5S)-and(-)-(1S, 5R)-2-Oxabicyclo [3.3.0]oct-6-en-3-one", *J.Med.Chem.*, vol. 33, pp. 1353–1360 (1990).

Chu et al., "An Efficient Total Synthesis of 3'-Azido-3'-Deoxythymidine (AZT) and 3'-Azido-2',3'-dideoxyuridine (AZDDU, CS-87) From D-Mannitol", *Tetrahedron Lett.*, vol. 29 (42), pp. 5349–5352 (1988).

Chu et al., "General Synthesis of 2',3'-Dideoxynucleosides And 2',3'-Didehydro-2',3'-Dideoxynucleosides", *J. Org. Chem.*, vol. 54, pp. 2217–2225 (1989).

Choi, et al., "In Situ Complexation Directs the Stereochemistry of N–Glycosylation in the Synthesis of Oxathiolanyl and Dioxolanyl Nucleoside Analogues", *J.Am. Chem. Soc.*, vol. 113, pp. 9377–9379 (1991).

Chu et al., "Synthesis And Structure–Activity Relationships Of 6–Substituted 2',3'-Dideoxypurine Nucleosides As Potential Anti–human Immunodeficiency Virus Agents", *J. Med. Chem.*, vol. 33, pp. 1553–1561 (1990).

Chu et al., "A Highly Stereoselective Glycosylation of 2-(Phenylselenenyl)-2,3-Dideoxyribose Derivative With Thymine: Synthesis Of 3'-Deoxy-2',3'-Didehydrothymidine And 3'-Deoxythymidine", *J. Org. Chem.*, vol. 55, pp. 1418–1420 (1990).

Chu et al., "Asymmetric Synthesis of Enantiomerically Pure (−)-(1'R,4'R)-Dioxolane-Thymine And Its Anti-HIV Activity", *Tetrahedron Lett.*, vol. 32(31), pp. 3791–3794 (1991).

Evans, et al. "Divergent Asymmetric Syntheses of Dioxolane Nucleoside Analogues", *Tetrahedron: Asymmetry*, vol. 4(11), pp. 2319–2322 (1993).

(List continued on next page.)

*Primary Examiner*—John Kight
*Assistant Examiner*—L. Eric Crane
*Attorney, Agent, or Firm*—Fish & Neave; James F. Haley, Jr.

[57] ABSTRACT

The present invention relates to highly diastereoselective processes for production of cis-nucleosides and nucleoside analogues and derivatives in high optical purity, and intermediates useful in those processes.

10 Claims, No Drawings

OTHER PUBLICATIONS

Farina and Benigni, "A New Synthesis Of 2',3'-Dideoxynucleosides For AIDS Chemotherapy", *Tetrahedron Lett.*, vol. 29(11), pp. 1239–1242 (1988).

Gosselin et al., "Systematic Synthesis And Biological Evaluation of α-and β-D-Lyxofuranosyl Nucleosides Of The Five Naturally Occurring Nucleic Acid Bases", *J. Med. Chem.*, vol. 30, pp. 982–991 (1987).

Herdewijn et al., "3'-Substituted 2',3'-Dideoxynucleoside Analogues as Potential Anti–HIV (HTLV–III/LAV) Agents", *J. Med. Chem.*, vol. 30, pp. 1270–1278 (1987).

Huryn et al., "Synthesis Of Iso–ddA, Member Of a Novel Class Of Anti–HIV Agents", *Tetrahedron Lett.*, vol. 30(46), pp. 6259–6262 (1989).

Huryn et al., "Synthesis of Iso–ddA, Member Of A Novel Class Of Anti–HIV Agents–Dioxolane–T. A New 2'3'–Dideoxynucleoside Prototype With In Vitro Activity Against HIV", *Chemtracts–Organic Chemistry*, vol. 3, pp. 249–251 (1990).

Jeong et al., "Asymmetric Synthesis and Biological Evaluation of β–L–(2R,5S)–and α–L–(2R,5R)–1,3–Oxathiolane–Pyrimidine and –Purine Nucleosides as Potential Anti–HIV Agents", *J. Med. Chem.*, vol. 36(2), pp. 181–195 (1993).

Kim, et al., "1,3–Dioxolanyl Purine Nucleosides (2R,4R) and (2R,4S5) with Selective Anti–HIV–1 Activity in Human Lymphocytes", *J. Med. Chem.*, vol. 36, pp. 30–37 (1993).

Kraus et al., "Synthesis of New 2,5–Substituted 1,3–Oxathiolanes. Intermediates in Nucleoside Chemistry", *Synthesis*, pp. 1046–1048 (1991).

Lin et al., "Synthesis and Antiviral Activity of Various 3'–Azido,3'–Amino, 2',3'–Unsaturated, and 2',3'–Dideoxy Analogues of Pyrimidine Deoxyribonucleosides Against Retroviruses", *J. Med. Chem.*, vol. 30, pp. 440–444 (1987).

Mansuri et al., "Preparation Of The Geometric Isomers Of DDC, DDA, D4C and D4T As Potential Anti–HIV Agents", *Bioorg. & Med. Chem. Lett.*, vol. 1(1), pp. 65–68 (1991).

Norbeck et al., "(±)-Dioxolane-T", *Tetrahedron Lett.*, vol. 30, pp. 6263–6266 (1989).

Okabe et al., "Synthesis Of The Dideoxynucleosides ddC And CNT From Glutamic Acid, Ribonolactone, And Pyrimidine Bases", *J. Org. Chem.*, vol. 53, pp. 4780–4786 (1988).

Seela and Muth, "Synthesis Of 4–Substituted 2–Aminopyrrolo[2,3–d] pyrimidine 2',3'–Dideoxyribonucleosides", *Liebigs Ann. Chem.*, pp. 227–232 (1990).

Siddiqui et al., "Antiviral Optically Pure Dioxolane Purine Nucleosides Analogues", *Bioorg. & Med. Chem. Lett.*, vol. 3(8), pp. 1543–1546 (1993).

Ueda and Watanabe, "Synthesis And Optical Properties Of 2,3–Dideoxy–D–Erythro–Hex–2–Enopyranosyl Nucleosides (Nucleosides And Nucleotides. LXII)", *Chem. Pharm. Bull.*, vol. 33(9), pp. 3689–3695 (1985).

Vedejs et al., "Method for Sulfide S–Benzylatian or S–Allylation Using Trimethylsilyl Triflate Activated Benzyl or Allyl Ethers", *J. Org. Chem.*, vol. 46, pp. 3353–3354 (1981).

Vince and Hua, "Synthesis And Anti–HIV Activity Of Carbocyclic 2',3'–Didehydro–2',3'–Dideoxy 2,6–Disubstituted Purine Nucleosides", *J. Med. Chem.*, vol. 33, pp. 17–21 (1990).

Wilson and Liotta, "A General method For Controlling Glycosylation Stereochemistry In The Synthesis Of 2'–Deoxyribose Nucleosides", *Tetrahedron Lett.*, vol. 31(13), pp. 1815–1818 (1990).

Wilson et al., "The Synthesis and Anti–HIV Activity of Pyrimidini Dioxolanyl Nucleosides", *Bioorg. Med. Chem. Lett.*, vol. 3(2), pp. 169–174 (1993).

M.N. Romanelli et al., "Enantioselectivity of Muscarinic Antagonists. 2,2-Dicyclohexyl-5-[(dimethylamino)methyl]-1,3-oxathiolane Methiodides and Related 3-oxides", *Journal of Medicinal Chemistry*, vol. 31, pp. 1698–1702 (1988).

PROCESSES FOR THE DIASTEREOSELECTIVE SYNTHESIS OF NUCLEOSIDE ANALOGUES

CROSS-REFERENCE TO RELATED APPLICATIONS

This application is a continuation-in-part of U.S. patent application Ser. No. 07/703,379, filed May 21, 1991 (now abandoned).

FIELD OF THE INVENTION

The present invention relates to diastereoselective processes for preparing optically active cis-nucleosides and nucleoside analogues and derivatives. The novel processes of this invention allow the stereo-controlled synthesis of a given enantiomer of a desired cis-nucleoside or nucleoside analogue or derivative in high optical purity. This invention also relates to novel intermediates useful in the processes of this invention.

BACKGROUND OF THE INVENTION

Nucleosides and their analogues and derivatives are an important class of therapeutic agents. For example, a number of nucleosides have shown antiviral activity against retroviruses such as human immunodeficiency virus (HIV), hepatitis B virus (HBV) and human T-lymphotropic virus (HTLV) (PCT publication WO 89/04662 and European Patent publication 0349242 A2). Among the nucleosides shown to have antiviral activity are 3'-azido-3'-deoxythymidine (AZT) and 2'3'-dideoxycytidine (DDC).

Most nucleosides and nucleoside analogues and derivatives contain at least two chiral centers (shown as * in formula (A)), and exist in the form of two pairs of optical isomers (i.e., two in the cis-configuration and two in the trans- configuration). However, generally only the cis-isomers exhibit useful biological activity.

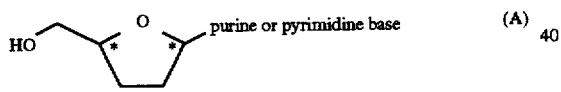

Different enantiomeric forms of the same cis-nucleoside may, however, have very different antiviral activities. M.M. Mansuri et al., "Preparation Of The Geometric Isomers Of DI)C, DDA, D4C and D4T As Potential Anti-HIV Agents", *Bioorg.Med.Chem. Lett.*, 1 (1), pp. 65–68 (1991). Therefore, a general and economically attractive stereoselective synthesis of the enantiomers of the biologically active cis-nucleosides is an important goal.

Many of the known processes for producing optically active nucleosides and their analogues and derivatives modify naturally occurring (i.e., optically active) nucleosides by altering the base or by altering the sugar via reductive procedures such as deoxygenation or radical initiated reductions. C.K. Chu et al., "General Synthesis Of 2 ', 3'-Dideoxynucleosides And 2'1,3'-Didehydro-2 ', 3'-Dideoxynucleos *J.Org.Chem.*, 54, pp. 2217–2225 (1989). These transformations involve multiple steps, including protection and deprotection and usually result in low yields. Moreover, they begin with and maintain the optical activity of the starting nucleoside. Thus, the nucleosides produced by these processes are limited to specific analogues of the enantiomeric form of the naturally occurring nucleoside. In addition, these procedures require the availability of the naturally occurring nucleoside, often an expensive starting material.

Other known processes for producing optically active nucleosides rely on conventional glycosylation procedures to add the sugar to the base. These procedures invariably give anomeric mixtures of cis- and trans-isomers which require tedious separation and result in lower yields of the desired biologically active cis-nucleoside. Improved glycosylation methods designed to yield only the cis-nucleoside require addition of a 2'- or 3'-substituent to the sugar. Because the 2'- or 3'-substituent is only useful in controlling cis-nucleoside synthesis in one configuration (when the 2' or 3' substituent is trans- to the 4' substituent), multiple steps are required to introduce this substituent in the proper configuration. The 2'- or 3'-substituent must then be removed after glycosylation, requiring additional steps. L. Wilson and D. Liotta, "A General Method For Controlling Glycosylation Stereochemistry In The Synthesis Of 2'-Deoxyribose Nucleosides", *Tetrahedron Lett.*, 31, pp. 1815–1818 (1990). Furthermore, to obtain an optically pure nucleoside product, the starting sugar must be optically pure. This also requires a series of time-consuming syntheses and purification steps.

SUMMARY OF THE INVENTION

The present invention overcomes the difficulties and shortcomings of the prior art and provides processes for producing optically active cis-nucleosides and nucleoside analogues and derivatives of formula (I)

wherein

W is O, S, S=O, $SO_2$, NZ, or $CH_2$;

X is O, S, S=O, $SO_2$, NZ, $CH_2$, CHF, CH, $CHN_3$, or CHOH:

Y is O, S, $CH_2$, CH, CHF, or CHOH;

Z is hydrogen, hydroxyl, alkyl or acyl.

$R_1$ is hydrogen or acyl; and $R_2$ is a purine or pyrimidine base or an analogue or derivative thereof;

provided that when Y is $CH_2$ and X is O, S, S=O, S, S=O or $SO_2$, W is not O, S, S=O or $SO_2$.

The processes of this invention comprise the step of glycosylating a desired purine or pyrimidine base or analogue or derivative thereof with a single enantiomer of the compound of formula (II)

wherein $R_3$ is a substituted carbonyl or carbonyl derivative and L is a leaving group. Glycosylation is accomplished using a Lewis acid of the formula (III)

wherein $R_5$, $R_6$, $R_7$, and $R_8$ are defined below and the resulting intermediate is reduced to give a nucleoside or nucleoside analogue or derivative of formula (I)

The processes of this invention have the advantages of allowing preparation of a nucleoside of formula (I) (or analogues or derivatives thereof) without using expensive starting materials, cumbersome protection and deprotection steps or addition and removal of 2'- or 3'-substituents. The processes of this invention produce nucleosides in high yields, with high purity and high optical specificity. The processes of this invention have the further advantage of generating nucleosides whose stereoisomeric configuration can be easily controlled simply by the selection o f the appropriate starting materials.

DETAILED DESCRIPTION OF THE INVENTION

In the processes for preparing optically active compounds of this invention in a configurational- and diastereo-selective manner, the following definitions are used:

$R_2$ is a purine or pyrimidine base or an analogue or derivative thereof.

A purine or pyrimidine base is a purine or pyrimidine base found in naturally occurring nucleosides. An analogue thereof is a base which mimics such naturally occurring bases in that their structures (the kinds of atoms and their arrangement) are similar to the naturally occurring bases but may either possess additional or lack certain of the functional properties of the naturally occurring bases. Such analogues include those derived by replacement of a CH moiety by a nitrogen atom, e.g., 5-azapyrimidines such as 5-azaicytosine) or vice versa (e.g., 7-deazapurines, such as 7-deazaadenine or 7-deazaguanine) or both (e.g., 7-deaza, 8-azapurines). By derivatives of such bases or analogues are meant those bases wherein ring substituents are either incorporated, removed, or modified by conventional substituents known in the art, e.g., halogen, hydroxyl, amino, $C_{1-6}$ alkyl. Such purine or pyrimidine bases, analogues and derivatives are well known to those skilled in the art.

A "nucleoside analogue or derivative" is a nucleoside which has been modified in any of the following or combinations of the following ways: base modifications, such as addition o:E a substituent (e.g., 5-fluorocytosine) or replacement of one group by an isosteric group (e.g., 7-deazaadenine); sugar modifications, such as substitution of the C-2 and C-3 hydroxyl groups by any substituent:, including hydrogen (e.g., 2 ', 3'-dideoxynucleosides), replacement of any ring CH group or the ring oxygen with a heteroatom; alteration of the site of attachment of the sugar to the base (e.g., pyrimidine bases usually attached to the sugar at the N-1 site may be, for example, attached at the N-3 or C-6 site and purines usually attached at the N-9 site may be, for example, attached at N-7); alteration of the site of attachment of the base to the sugar (e.g., the base may be attached to the sugar at C-2, such as iso-DDA); or alteration of configuration of the sugar-base linkage (e.g., cis or trans configurations).

$R_3$ is a carbonyl substituted with hydrogen, hydroxyl, trialkylsilyl, trialkylsiloxy, $C_{1-30}$ alkyl, $C_{7-30}$ aralkyl, $C_{1-30}$ alkoxy, $C_{1-30}$ amine (primary, secondary or tertiary), $C_{1-30}$ thiol; $C_{6-20}$ aryl; $C_{1-20}$ alkenyl; $C_{1-20}$ alkynyl; 1,2-dicarbonyl, such as

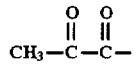

substituted with $C_{1-6}$ alkyl or $C_{6-20}$ aryl; anyhdrides such as

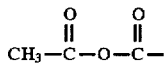

substituted with $C_{1-6}$ alkyl or $C_{6-20}$ aryl; azomethine substituted at nitrogen with hydrogen, $C_{1-20}$ alkyl or $C_{1-10}$ alkoxy or $C_{1-10}$ dialkylamino or at carbon with hydrogen, $C_{1-20}$ alkyl, or $C_{1-20}$ alkoxy; thiocarbonyl (C=S) substituted with hydroxyl, $C_{1-20}$ alkoxy, or $C_{1-20}$ thiol; a homologue of carbonyl, e.g.,

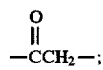

a homologue of thiocarbonyl, e.g.,

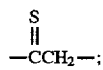

or a homologue of azomethine, such as

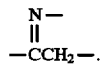

The preferred substituted carbonyl/carbonyl derivatives are alkoxycarbonyls, such as methyl, ethyl, isopropyl, t-butyl and menthyl; carboxyls; diethyl-carboxamidle; pyrrolidine amide; methyl ketone and phenyl ketone. The more preferred substituted carbonylcarbonyl derivatives are esters and carboxyls and the most preferred are esters.

$R_4$ is a chiral auxiliary. The term "chiral auxiliary" describes asymmetric molecules that are used to effect the chemical resolution of a racemic mixture. Such chiral auxiliaries may possess one chiral center such as methylbenzylamine or several chiral centers such as menthol. The purpose of the chiral auxiliary, once built into the starting material, is to allow simple separation of the resulting diastereomeric mixture. See, for example, J. Jacques et al., *Enantiomers, Racemates And Resolutions*, pp. 251–369, John Wiley & Sons, New York (1981).

$R_5$, R6 and $R_7$ are independently selected from the group consisting of hydrogen, $C_{1-20}$ alkyl (e.g., methyl, ethyl, t-butyl), optionally substituted by halogens (F, Cl, Br, I), $C_{1-6}$ alkoxy (e.g., methoxy) or $C_{6-20}$ aryloxy (e.g., phenoxy); $C_{7-20}$ aralkyl (e.g., benzyl), optionally substituted by halogen, $C_{1-20}$ alkyl or $C_{1-20}$ alkoxy (e.g., p-methoxybenzyl); $C_{6-20}$ aryl (e.g., phenyl), optionally substituted by halogens, C alkyl or $C_{1-20}$ alkoxy; trialkylsilyl; halogens (F, Cl, Br, I).

$R_8$ is selected from the group consisting of halogen (F, Cl, Br, I); $Ck_{1-20}$ sulphonate esters, optionally substituted by halogens (e.g., trifluoro-methane sulphonate); $C_{1-20}$ alkyl esters, optionally substituted by halogen (e.g., trifluoroacetate); polyvalent: halides (e.g., triiodide); trisubstituted silyl groups of the general formula $(R_5)(R_6)(R_7)Si$ (wherein $R_5$, $R_6$, and $R_7$ are as defined above); saturated or unsaturated selenenyl $C_{6-20}$ aryl; substituted or unsubstituted $C_{6-20}$ arylsulfenyl; substituted or unsubstituted $C_{1-20}$ alkoxyalkyl; and trialkylsiloxy.

L is a "leaving group", i.e., an atom or a group which is displaceable upon reaction with an appropriate purine or pyrimidine base, with or without the presence of a Lewis acid. Suitable leaving groups include acyloxy groups, alkoxy groups, e.g., alkoxy carbonyl groups such as ethoxy carbonyl; halogens such as iodine, bromine, chlorine, or fluorine; amido; azido; isocyanato; substituted or unsubstituted, saturated or unsaturated thiolates, such as thiomethyl or thiophenyl; substituted or unsubstituted, saturated or unsaturated seleno, seleninyl, or selenonyl compounds, such as phenyl selenide or alkyl selenide.

A suitable leaving group may also be —OR, where R is a substituted or unsubstituted, saturated or unsaturated alkyl group, e.g., $C_{1-6}$ alkyl or alkenyl group; a substituted or unsubstituted aliphatic or aromatic acyl group, e.g., a $C_{1-6}$ aliphatic acyl group such as acetyl and a substituted or unsubstituted aromatic acyl group such as benzoyl; a substituted or unsubstituted, saturated or unsaturated alkoxy or aryloxy carbonyl group, such as methyl carbonate and phenyl carbonate; substituted or unsubstituted sulphonyl imidazolide; substituted or unsubstituted aliphatic or aromatic amino carbonyl group, such as phenyl carbamate; substituted or unsubstituted alkyl imidiate group such as trichloroacetamidate; substituted or unsubstituted, saturated or unsaturated phosphonate, such as diethylphosphonate; substituted or unsubstituted aliphatic or aromatic sulphinyl or sulphonyl group, such as tosylate; or hydrogen.

As used in this application, the term "alkyl" represents a substituted (by a halogen, hydroxyl or $C_{6-20}$ aryl) or unsubstituted straight chain, branched chain, or cyclic hydrocarbon moiety having 1 to 30 carbon atoms and preferably, from 1 to 6 carbon atoms.

The terms "alkenyl" and "alkynyl" represent substituted (by a halogen, hydroxyl or $C_{6-20}$ aryl) or unsubstituted straight, branched or cyclic hydrocarbon chains having 1 to 20 carbon atoms and preferably from 1 to 5 carbon atoms and containing at least one unsaturated group (e.g., allyl).

The term "alkoxy" represents a substituted or unsubstituted alkyl group containing from 1 to 30 carbon atoms and preferably from 1 to 6 carbon atoms, wherein the alkyl group is covalently bonded to an adjacent element through an oxygen atom (e.g., methoxy and ethoxy).

The term "amine" represents alkyl, aryl, alkenyl, alkynyl, or aralkyl groups containing from 1 to 30 carbon atoms and preferably 1 to 12 carbon atoms, covalently bonded to an adjacent element through a nitrogen atom (e.g., pyrrolidine). They include primary, secondary and tertiary amines and quaternary ammonium salts.

The term "thiol" represents alkyl, aryl, aralkyl, alkenyl or alkynyl groups containing from 1 to 30 carbon atoms and preferably from 1 to 6 carbon atoms, covalently bonded to an adjacent element through a sulfur atom (e.g., thiomethyl).

The term "aryl" represents a carbocyclic moiety which may be substituted by at least one heteroatom (e.g., N, 0, or S) and containing at least one benzenoid-type ring and preferably containing from 6 to 15 carbon atoms (e.g., phenyl and naphthyl).

The term "aralkyl" represents an aryl group attached to the adjacent atom by an alkyl (e.g., benzyl).

The term "alkoxyalkyl" represents an alkoxy group attached to the adjacent group by an alkyl group (e.g., methoxymethyl).

The term "aryloxy" represents a substituted (by a halogen, trifluoromethyl or $C_{1-5}$ alkoxy) or unsubstituted aryl moiety covalently bonded through an oxygen atom (e.g., phenoxy).

The term "acyl" refers to a radical derived from a carboxylic acid, substituted (by a halogen (F, Cl, Br, I), $C_{6-20}$ aryl or $C_{1-6}$ alkyl) or unsubstituted, by replacement of the -OH group. Like the acid to which it is related, an acyl radical may be aliphatic or aromatic, substituted (by a halogen, $C_{1-5}$ alkoxyalkyl, nitro or $O_2$) or unsubstituted, and whatever the structure of the rest of the molecule may be, the properties of the functional group remain essentially the same (e.g., acetyl, propionyl, isobutanoyl, pivaloyl, hexanoyl, trifluoroacetyl, chloroacetyl, and cyclohexanoyl).

A key feature of the processes of this invention is the use of a substituted carbonyl or carbonyl derivative as $R_3$ instead of a protected hydroxymethyl group as previously described in the art. Surprisingly, the substituted carbonyl or carbonyl derivative is not cleaved by exposure to a Lewis acid, as would have been expected by one of skill in the art when a Lewis acid of formula (III) is added to a mixture of silylated purine or pyrimidine base and the sugar compound of formula (II). Instead, the substituted carbonyl/carbonyl derivative in the intermediate of formula (VI) forces the purine or pyrimidine base ($R_2$) to add in the cis-configuration relative to the substituted carbonyl/carbonyl derivative group. Without a substituted carbonyl or carbonyl derivative attached to C4' (for example, when a hydroxyitiethyl group is instead used), the coupling procedures described in Step 4 below will result in a mixture of cis- and trans-isomers.

Another key feature of the processes of this invention is the choice of Lewis acid. The Lewis acids used in the preparation of compounds of formula (I) have the general formula (III)

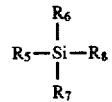

wherein $R_5$, $R_6$, $R_7$ and $R_8$ are as defined previously. These Lewis acids may be generated in situ or prepared using any method known in the art (e.g., A.H. Schmidt, "Bromotrimethylsilane and Iodotrimethylsilane-Versatile Reagents for Organic Synthesis", *Aldrichimica Acta*, 14, pp. 31–38 (1981). The preferred Lewis acids of this invention are iodotrimethylsilane and trimethylsilyl triflate. The preferred $R_5$, R6 and $R_7$ groups are methyl or iodine. The most preferred $R_5$, $R_6$ and $R_7$ group is methyl. The preferred $R_8$ groups are iodine, chlorine, bromine or sulphonate esters. The most preferred $R_8$ groups are iodine and trifluoromethane sulphonate.

In the preferred process of this invention, cis- and trans-isomers of a sugar of formula (II)

are separated by fractional crystallization and the desired configurational isomer selected. The selected cis- or the trans-isomer may then be chemically resolved using a chiral auxiliary. The pure chiral auxiliary-sugar diastereomer is then coupled to a silylated purine or pyrimidine base in the presence of a Lewis acid to afford an optically active nucleoside of cis- configuration which is subsequently reduced to give a nucleoside of formula (I).

Schemes 1A and 1B depict this preferred process as applied to any nucleoside of formula (I).

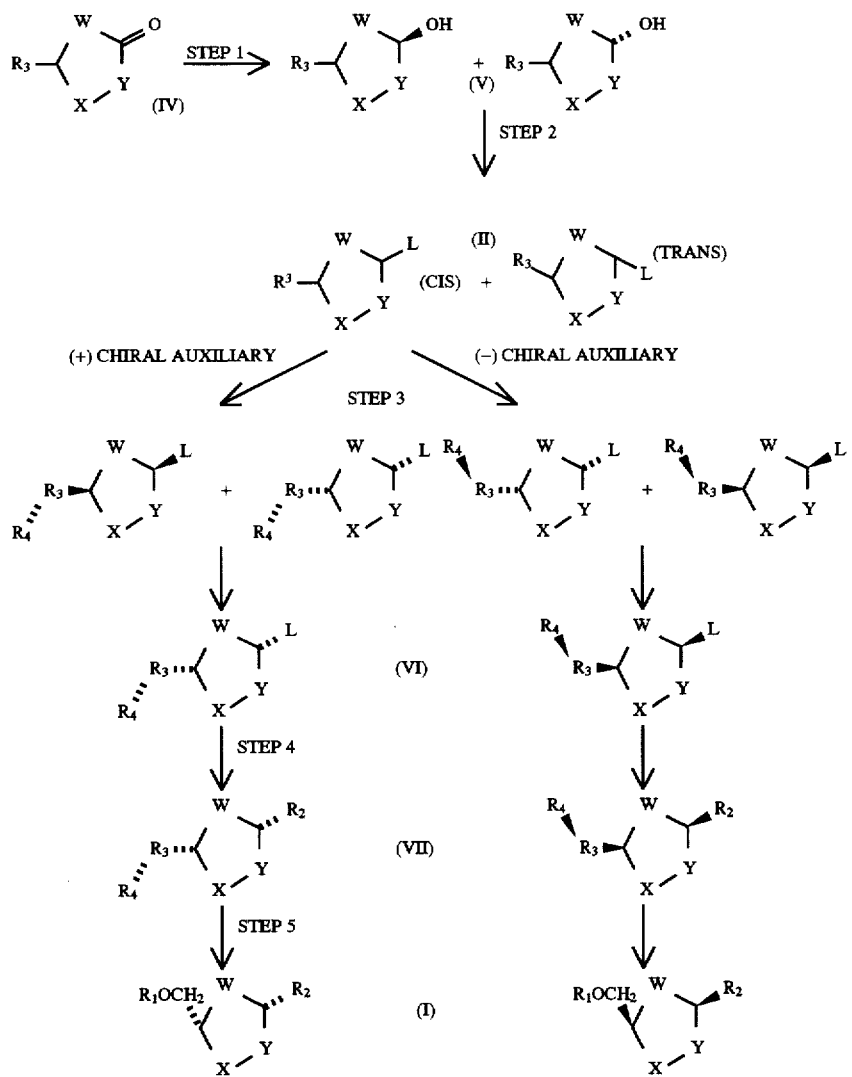
SCHEME 1A
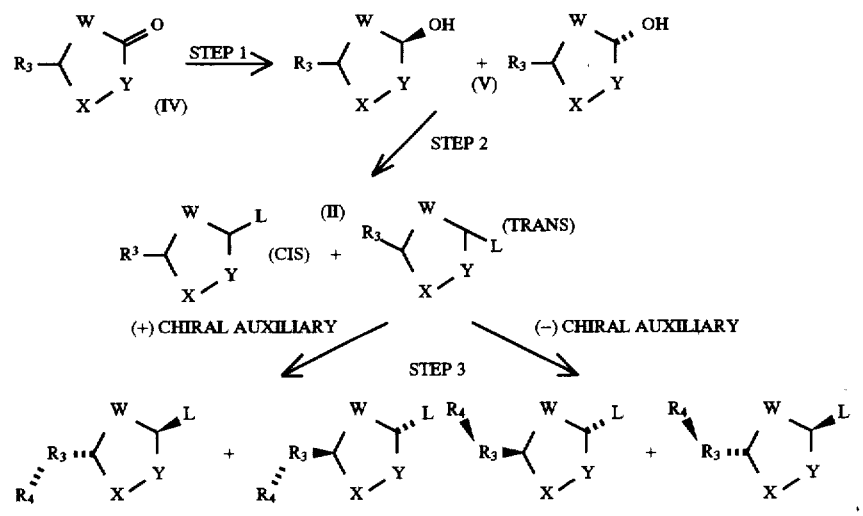
SCHEME 1B

-continued
SCHEME 1B

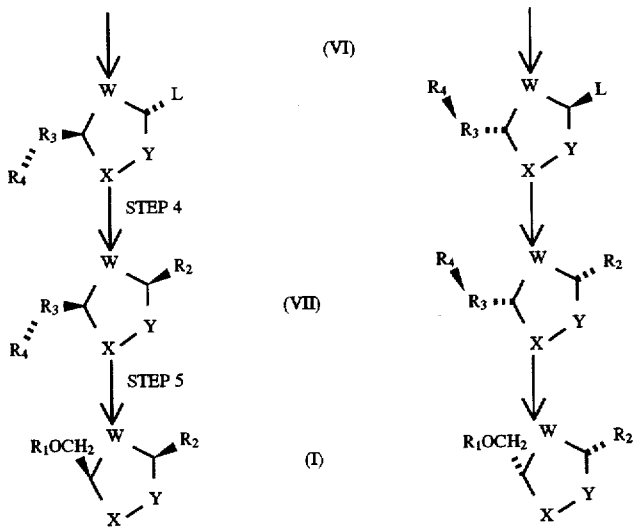

The various steps as illustrated in Schemes 1A and 1B may be briefly described as follows:

Step 1: The starting carbonyl-sugar of formula (IV) can be prepared by any method known in the art. E.g., Farina and Benigni, "A New Synthesis Of 2,3'-Dideoxy-nucleosides For Aids Chemotherapy", *Tetrahedron Letters*, 29, pp. 1239–1242 (1988) and M.

Okabe et al. "Synthesis Of The Dideoxynucleosides ddC and CNT From Glutamic Acid, Ribonolactone and Pyrimidine Bases", *J. Org. Chem.*, 53, pp. 4780–4786 (1988). The carbonyl group of this starting compound is reduced chemoselectively with a suitable reducing agent, such as disiamylborane to give the cis- and trans-isomers of formula (V). Ordinarily, less cis-isomer is produced than trans.

Step 2: The hydroxyl group in the intermediate of formula (V) is readily converted to a leaving group by any method known in the art (e.g., T.W. Greene *Protective Groups In Organic Synthesis*, pp. 50–72, John Wiley & Sons, New York (1981)) to give the novel intermediates of formula (II).

This anomeric mixture is then separated by fractional crystallization into the two configurational isomers. The solvent may be adjusted to select for either the cis- or trans-isomer. D.J. Pasto and C.R. Johnson, *Organic Structure Determination*, pp. 7–10, Prentice-Hall, Inc., New Jersey (1969).

Step 3: Either the cis- (Scheme 1A) or trans-isomer (Scheme 1B) of formula (II) is chemically resolved using a chiral auxiliary (R) A suitable chiral auxiliary is one of high optical purity and where the mirror image is readily available, such as d- and l-menthol. The resulting diastereomers of formula (VI) are easily separated by fractional crystallization. Alternatively, either the cis- or the trans-isomer may be resolved enzymatically or by other methods known in the art. J. Jacques et al., *Enantiomers, Racemates And Resolutions*, pp. 251–369, John Wiley & Sons, New York (1981).

The optical purity of the diastereomer (VI, VII or I) can be determined by chiral HPLC methods, specific rotation measurements and NMR techniques. If the opposite enantiomer is desired, it may be obtained by using the mirror image of the chiral auxiliary initially employed. For example, if the chiral auxiliary d-menthol produces a (+)-enantiomer nucleoside, its mirror image, l-menthol, will produce the (-)-enantiomer.

Step 4: A previously silylated (or silylated in situ) purine or pyrimidine base or analogue or derivative thereof is then glycosylated with the resulting pure diastereomer in the presence of a Lewis acid of formula (III), such as iodotrimethylsilane (TMSI) or trimethylsilyl triflate (ThSOTf), to give a nucleoside of cis-configuration of formula (VII). This nucleoside is optically active and is substantially free of the corresponding trans-isomer (i.e., it contains no more than 25%, preferably no more than 10% and more preferably no more than 5% of the trans-isomer). coupling of the intermediate of formula (VI) to the purine or pyrimidine base in this step proceeds in higher yields with the cis-isomer.

The preferred silylating agent for pyrimidine bases is t-butyldimethylsilyl triflate. It is believed that the bulky t-butyl group increases yields by weakening the interaction between the Lewis acid and silylated pyrimidine base.

The preferred method of mixing reagents in Step 4 is to first add the chiral auxiliary-sugar of formula (VI) to the silylated purine or pyrimidine base. The Lewis acid of formula (III) is then added to the mixture.

Step 5: The cis-nucleoside obtained in Step 4 may then be reduced with an appropriate reducing agent to remove the chiral auxiliary and give a specific stereoisomer of formula (I). The absolute configuration of this stereoisomer corresponds to that of the nucleoside intermediate of formula (VII). As shown in Scheme 1, either the cis- (Scheme 1A) or the trans-isomers (Scheme 1B) obtained in Step 2 will yield a cis end product.

A second process for the diastereoselective synthesis of compounds of formula (I) is illustrated by Scheme 2. The process of Scheme 2 is useful when optically pure starting material may be readily obtained commercially or easily prepared by known methods.

The optically active starting material is chemoselectively reduced and the resulting hydroxyl group converted to a leaving group. The diastereomeric mixture may be carried on further to compounds of formula (I) in a manner analogous to that described in Scheme 1. Optionally, the diastereomeric mixture may be separated by fractional crystallization and each isolated optically active diastereomer may be carried on further to compounds of formula (I).

Scheme 2 depicts the second process of this invention as applied to any nucleoside.

SCHEME 2

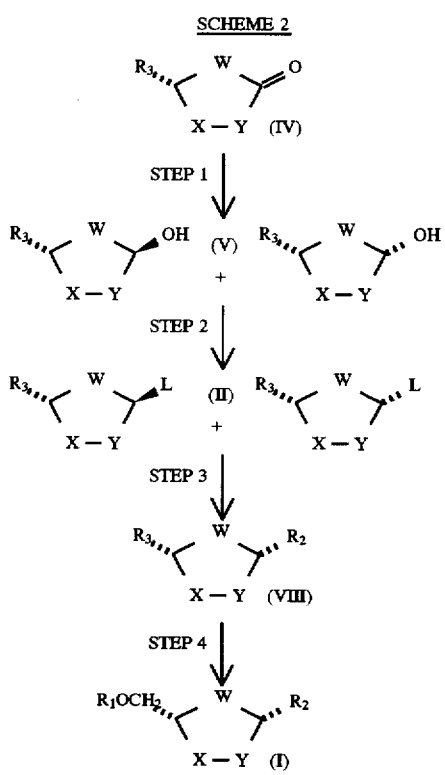

The various steps involved in the synthesis of the nucleosides of formula (I) as depicted in Scheme 2 may be briefly described as follows:

Step 1: The starting material of formula (IV) may be obtained commercially in optically pure form or prepared according to the procedures of Farina and Benigni, "A New Synthesis Of 2,3'-Dideoxy-nucleosides For Aids Chemotherapy", *Tetrahedron Letters*, 29, pp. 1239–1242 (1988) and M. Okabe et al. "Synthesis Of The Dideoxynucleosides ddC and CNT From Glutamic Acid, Ribonolactone and Pyrimidine Bases", *J. Org. Chem.*, 53, pp. 4780–4786 (1988). The single isomer of formula (IV) is chemoselectively reduced by a suitable reducing agent, such as disiamylborane to give a mixture of two diastereomers of formula (V).

Step 2: The hydroxyl groups of the two diastereomers of formula (V) are converted to leaving groups by any method known in the art to give a mixture of two diastereomers of formula (II).

Step 3: The diastereomeric mixture of formula (II) is reacted with previously silylated (or silylated in situ) purine or pyrimidine base or analogue or derivative. Then, addition of a Lewis acid of formula (III), such as iodotrimethylsilane (TMSI) or trimethylsilyl triflate (TMSOTf) yields a nucleoside of cis-configuration of formula (VIII). This nucleoside is substantially free of the corresponding trans-isomer.

Step 4: The optically active cis-nucleoside of formula (VIII) is reduced stereospecifically with a reducing agent preferably lithium triethylborohydride or lithium aluminum hydride and more preferably sodium borohydride in an appropriate solvent such as tetrahydrofuran or diethyl ether to give the compound of formula (I).

Alternatively, at the end of Step 2, either the cis-or the trans-isomer may be separated out of the diastereomeric mixture of formula (II) by fractional crystallization or chromatography. The solvent may be adjusted to select for either the cis- or the trans-isomer. The single diastereomer of formula (II) would then be carried forward as described in Steps 3 and 4 to a compound of formula (I).

Schemes 3, 4 and 5 illustrate the application of the process of Scheme 2 to the synthesis of the enantiomers of cis-dideoxynucleoside analogues.

Although the process is illustrated using specific reacents and starting materials, it will be appreciated by one of skill in the art that suitable analogous reactants and starting materials may be used to prepare analogous compounds.

SCHEME 3

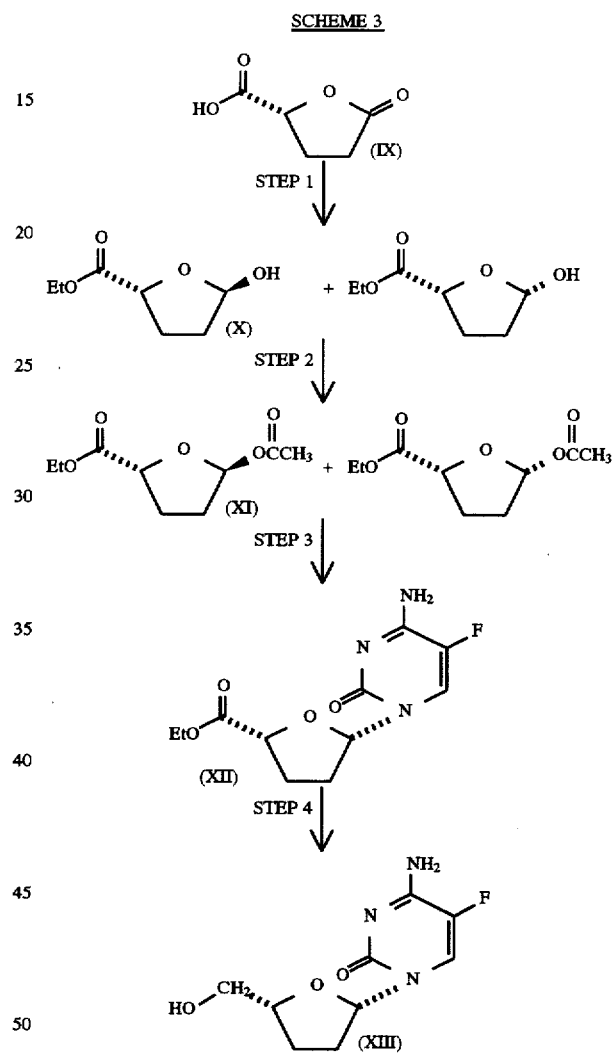

The various steps illustrated in Scheme 3 may be briefly described as follows:

Step 1: The starting material (2R)-5-oxo-2-tetrahydrofuran carboxylic acid (IX) is available from commercial sources or by synthesis from D-glutamic acid M. Okabe et al. "Synthesis Of The Dideoxynucleosides ddC and CNT From Glutamic Acid, Ribono-lactone and Pyrimidine Bases", *J. Org. Chem.*, 53, pp. 4780–4786 (1988). The starting material is esterified with an alcohol such as ethanol in the presence of an acylating agent such as oxalyl chloride and an esterification catalyst such as 4-dimethylaminopyridine and a base such as pyridine in a compatible solvent such as dichloromethane. The esterified compound is reduced with an appropriate reducing agent such as disiamylborane in a compatible organic solvent, such as tetrahydrofuran (A. Pelter et al., "Borane Reagents", *Academic Press*, p. 426 (1938)), to give the compounds of formula (X).

Step 2: The compounds of formula (X) is reacted with an acid chloride or acid anhydride, such as acetic anhydride, in the presence of pyridine and an acylation catalyst, such as 4-dimethylaminopyridine, to give the compounds of formula (XI).

Step 3: The mixture of cis- and trans-acetoxy compound of formula (XI) is reacted with 5-fluorocytosine or other pyrimidine base or analogue thereof. The purine or pyrimidine base or analogue is preferably silated with hexamethyldisilazane or more preferably silylated in situ with t-butyldimethylsilyl triflate in a compatible organic solvent, such as dichloromethane containing a hindered base, preferably 2,4,6-collidine.

A Lewis acid, preferably one derived from the compounds of formula (III), more preferably iodotrimethylsilane or trimethyl-silyl triflate, is then added to give the cis compound of formula (XII) in a highly diastereoselective manner.

Step 5: The optically active cis-nucleoside (with some trans- isomer) of formula (XII) is reduced stereospecifically with a reducing agent, preferably sodium borohydride in an appropriate solvent, such as ethanol to gives after purification, the compound of formula (XIII).

It will be appreciated by one of skill in the art that if the enantiomer of formula (XIII) is desired, the starting material of formula (IX) would be (2S)-5-oxo-2-testrahydrofuran carboxylic acid (Scheme 4) and the process would proceed just as described for Scheme 3.

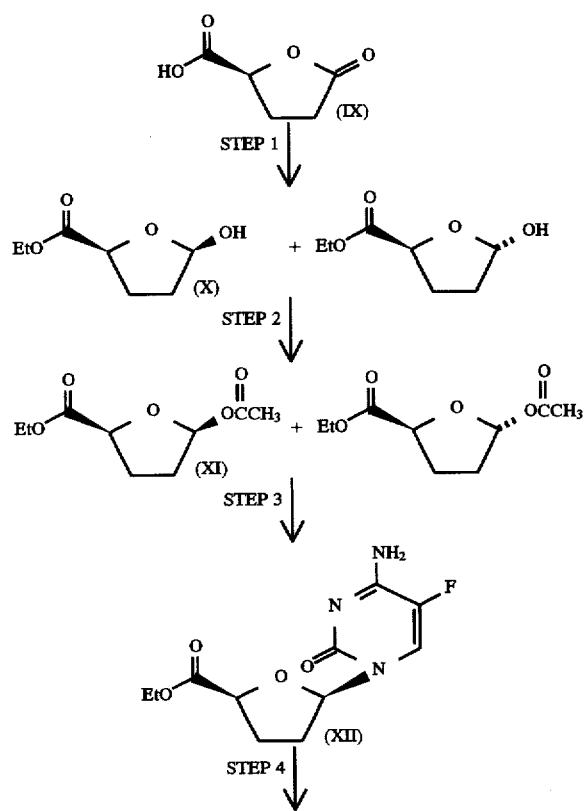

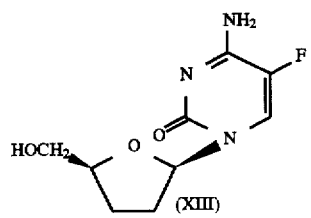

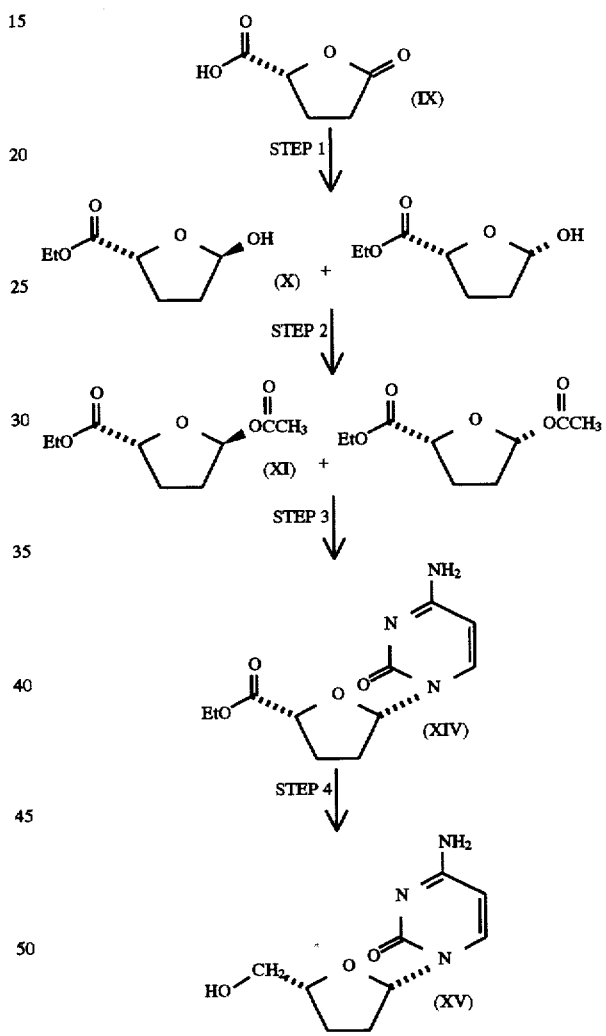

The various steps illustrated in Scheme 5 may be briefly described as follows:

Step 1: The starting material (2R)-5-oxo-2-tetrahydrofuran carboxylic acid (IX) is esterified with an alcohol such as ethanol in the presence of an acylating agent such as oxalyl chloride and an esterification catalyst such as 4-dimethylamino-pyrimidine and a base such as pyridine in a compatible solvent such as dichloromethane. The esterified compound is reduced with an appropriate reducing agent such as disiamylborane in a compatible organic solvent, such as tetrahydrofuran to give the compounds of formula (X).

Step 2: The compounds of formula (X) is reacted with an acid chloride or acid anhydride, such as acetic anhydride, in the presence of pyridine and an acylation catalyst, such as 4-dimethylaminopyridine, to give the compounds of formula (XI).

Step 3: The mixture of cis- and trans-acetoxy compound of formula (XI) is reacted with N-acetyl cytosine or other pyrimidine base or analogue thereof. The purine or pyrimidine base or analogue is preferably silated with hexamethyldisilazane or more preferably silylated in situ with trimethylsilyl triflate in a compatible organic solvent, such as dichloromethane containing a hindered base, preferably 2,4,6-collidine.

A Lewis acid, preferably one derived from the compounds of formula (III), more preferably iodotrimethylsilane, is then added to give cis nucleoside in a highly diastereoselective manner. The pure cis- nucleoside is obtained by trituration with an appropriate sulvent such as ethyl acetate and hexanes.

The N-acetyl group is hydrolyzed preferably under acidic conditions and more preferably with trifluoroacet.ic acid in a compatible organic solvent such as isopropanol, preferably under reflux, to give the deacylated compounds of formula (XIV).

Step 4: The optically active cis-nucleoside of formula (XIV) is reduced stereospecifically with a reducing agent, preferably sodium borohydride in an appropriate solvent, such as ethanol to give the compound of formula (XV). 10 In the diastereoselective processes of this invention, the following intermediates are of particular importance:

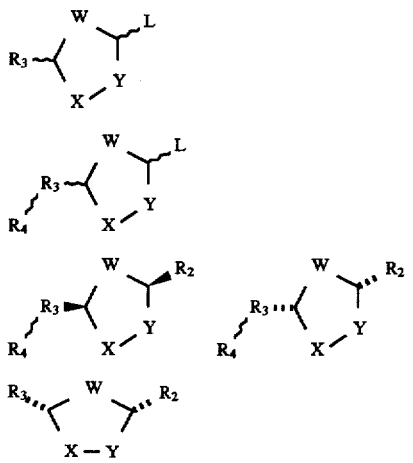

wherein R$_3$, R$_4$ and L are as defined above;
  cis and trans-2R-carboethoxy-5-hydroxytetra-hydrofuran;
  cis and trans-2S-carboethoxy-5-hydroxytetra-hydrofuran;
  cis and trans-2R-carboethoxy-5-acetoxytetra-hydrofuran;
  cis and trans-2S-carboethoxy-5-acetoxytetra-hydrofuran;
  1'S-(N-4-acetylcytosin-1-yl)-4'R-carboethoxytetrahydrofuran;
  1'S-(cytosin-1-yl)-4'R-carboethoxytetra-hydrofuran;
  1'R-(5-fluorocytosin-1-yl)-4'S-carboethoxytetrahydrofuran and 1'S-(5-fluorocytosin-1-yl)-4'S-carboethoxytetrahydrofuran; and
  1' S-(5-fluorocytosin-1-yl)-4' R-carboethoxytetrahydrofuran and 1' R-(5-fluorocytosin-1-yl)-4' R-carboethoxytetrahydrofuran.

The following examples illustrate the present invention in a manner of which it can be practiced but, as such, should not be construed as limitations upon the overall scope of the processes of this invention. Except where specifically noted, all [α]$_D$ measurements were recorded at ambient temperature.

EXAMPLE 1

2R-CARBOETHOXY-5-OXO-TETRAHYDROFURAN

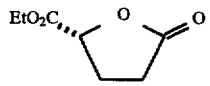

To a cold (0° C.) stirred solution of 5-oxo-2R-tetrahydrofurancarboxylic acid (3 g, 23 mmol), 4-dimethylaminopyridine (141 mg, 0.05 equivalents), and pyridine (3.92 mL, 2.1 equivalents) in dichloromethane (15 mL) under an argon atmosphere was added oxalyl chloride (2.11 mL, 1.05 equivalents) over a period of 30 minutes. The cooling bath was removed and the reaction mixture was stirred at room temperature for 10 minutes. Ethanol (2.0 mL, 1.5 equivalents) was introduced and stirring was continued for another 1 hour 40 minutes. The reaction mixture was diluted with water and dichloromethane, followed by stirring for 10 minutes. The resultant mixture was transferred to a separatory funnel. The aqueous phase was removed and the organic layer was washed with 1 M HCl, saturated NaHCO$_3$, brine, and then was dried (Na$_2$SO$_4$). The solvent was evaporated under reduced pressure and the crude product thus obtained was subjected to column chromatography (1:1 EtOAc-Hexane) to afford 3.23 g of the desired product as a syrup. $^1$H NMR (CDCl$_3$):δ 1.28 (t, 3H, J=7.1 Hz), 2.20–2.40 (m, $^1$H), 4.23 (d of q 2H, J=0.9, 7.1 Hz), 4.86–4.96 (m 1H).

EXAMPLE 2

CIS AND TRANS-2R-CARBOETHOXY-5-HYDROXYTETRAHYDROFURAN

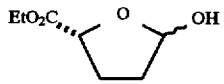

A solution of disiamylborane was prepared by mixing 35 mL of BH$_3$ THF (1 M in THF) and 35 mL of 2-methyl-2-butene (2 M in THF) at 0° C. followed stirring at 0° C. for 75 minutes. To this solution was introduced 2R-carboethoxy-5-oxotetrahydrofuran dissolved in THF (6 mL). The resultant mixture was allowed to warm slowly to room temperature over a period of 2.5 hours and then was stirred for another 15 hours. Saturated ammonium chloride solution was added, followed by dilution with EtOAc. The above mixture was stirred for 10 minutes and then was transferred to a separatory funnel. The organic phase was washed successively with saturated NH$_4$Cl, brine, and then was dried (Na$_2$SO$_4$). The solvent was removed on a rotary evaporator and the crude product obtained was purified by column chromatography (40% EtOAc-Hexanes). The desired products were isolated in 70% yield (2.05 g) as a 2:3 mixture of isomer epimeric at C5. Trace amount of the open form isomer was also detected ($^1$H NMR). The title compounds displayed the following spectral characteristics: $^1$H NMR (CDCl$_3$): δ 1.28 (t, 2H, J=7.1 Hz), 1.30 (t, 1H, J=7.1 Hz), 1.85–2.70 (m, 4H), 2.59 -(d, 0.33H, J=5.5 Hz), 2.88 (d, 0.67H, J=3.1 Hz), 4.154.65 (m, 2H), 4.57 (d of d, 0.33H, J=6.4, 8.3 Hz), 4.70 (d of d, 0.67H, J=4.1, 8.7 Hz), 5.59 (m, 0.33H), 5.74 (m, 0.67H).

EXAMPLE 3

CIS AND TRANS- 2R-CARBOETHOXY-5-ACETOXYTETRAHYDROFURAN

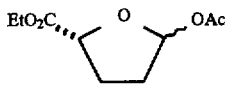

To a cold (−78° C.) stirred solution of a 2:3 mixture of cis and trans-2R-carboethoxy-5-hydroxytetra- hydrofuran (2.04 g, 12.75 mmol), pyridine (1.24 mL, 1.2 equivalents), and 4-dimethylaminopyridine (16 mg, 0.01 equivalent) in dichloromethane (20 mL) was added acetyl chloride (1.09 mL, 1.2 equivalents) over a period of 5 minutes. The resultant mixture was stirred for 10 minutes. The −78° C. cooling bath was then replaced with an ice-water bath. Stirring was continued for 4.5 hours while the bath temperature was allowed to warm slowly to room temperature. The reaction mixture was diluted with dichioromethane and then was transferred to a separatory funnel. The organic layer was washed successively with water, 1 M HCl, saturated $NaHCO_3$, brine and then was dried ($Na_2SO_4$). The solvent was removed on a rotary evaporator and the crude product obtained was purified by column chromatography (40% EtOAc-Hexane) to provide 1.757 g of the title compounds (a 5:4 mixture) as a thick oil. $^1$H NMR ($CDCl_3$); δ 1.28 (t, 1.68H, J=7.1 Hz), 1.29 (t, 1.32H, J=7.1 Hz), 1.90-2.30 (m, 3H), 2.30-2.50 (m, 1H), 4.10-4.30 (m, 2H), 4.59 (t, 0.44H, J=8.0 Hz), 4.70 (d of d, 0.56H, J=3.2, 8.9 Hz), 6.33 (d of d, 0.44H, J=1.1, 3.9 Hz), 6.46 (d, 0.56H, J=4.5 Hz).

EXAMPLE 4

1'S-(N-4-ACETYLCYTOSIN-1-YL)-4' R-CARBOETHOXYTETRA-HYDROFURAN

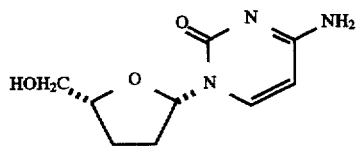

To a stirred suspension of N-4-acetylcytosine (50 mg, 0.298 mmol) in dichloromethane (0.75 mL) containing 2,6-lutidine (35 μL, 0.298 mmol) under an argon atmosphere was added trimethylsilyl trifluoromethanesulphonate (58 μL, 0.298 mmol). The resulting mixture was stirred for 15 minutes to give a light suspension. A solution of a 5:4 mixture of cis- and trans-2R-carboethoxy-5-acetoxytetrahydrofuran (50 mg, 0.248 mmol) in dichloromethane (1 mL) and iodotrimethylsilane (35 μL, 0.248 mmol) was sequentially introduced into the above suspension to generate a homogeneous solution. The reaction was allowed to proceed at room temperature for 1 hour and 40 minutes and then was quenched with a half-saturated solution of $Na_2S_2O_3$. The resulting mixture was stirred for 5 minutes and then was transferred to a separatory funnel with the aid of more dichloromethane. The aqueous phase was removed and the organic layer was washed with saturated $Na_2S_2O_3$ water, brine and then was dried ($Na_2SO_4$). The combined aqueous washings were reextracted with dichloromethane. The organic extracts were combined and concentrated under reduced pressure to provide 83 mg of the crude product. $^1$H NMR analysis of the crude product indicated that a cis and trans (4:1) mixture of the expected nucleosides was generated. The crude product was dissolved in a minimum amount of chloroform. Addition of a 3:7 mixture of EtOAc-hexanes into this solution produced a white precipitate which was collected by suction filtration. Drying of this solid under vacuum afforded 25 mg (32%) of the title compound. $^1$H NMR (CDCl): δ 1.33 (t, 3H, J=7.1 Hz), 1.90-2.08 (m, 1H), 2.08-2.30 (m, 1H), 2.23 (s, 3H), 4.20-4.40 (m, 2H), 4.64 (t, 1H, J=7.2 Hz), 6.15 (d of d, 1H, J=4.0, 5.9 Hz), 7.46 (d, 1H, J=7.5 Hz), 8.34 (br s, $^1$H), 8.82 (d, $^1$H, J=7.5 Hz).

The washing was concentrated to give 58 mg of a cis and trains mixture (5:2) of the title compound and its 1' isomer.

EXAMPLE 5

β-L-2' 3' -DIDEOXYCYTIDINE

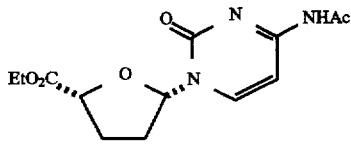

A mixture of 1' S-(N-4-acetylcytosin-1-yl)- 4' R-carboethoxytetrahydrofuran (49 mg, 0.158 mmol, contains ca. 4% of the corresponding 1' R isomer) and trifluoroacet:ic acid (24 μL, 2 equivalents) in ethanol (1 mL) was refluxed under an argon atmosphere for 2 hours and 40 minutes. The resultant mixture consisting of 1' S-(cytosine-1-yl)-4' R-carboethoxytetrahydrofuran and its 1' epimer was cooled to room temperature and then was diluted with ethanol (0.5 mLT). Sodium borohydride (18 mg, 3 equivalents) was introduced and the reaction mixture was stirred for 1.5 hours. More reducing agent (6 mg) was added and stirring was continued for another 1 hour 20 minutes. The reaction was quenched by the addition of 2 drops of concentrated ammonium hydroxide followed by rigorous stirring for 15 minutes. The solvent was evaporated under reduced pressure and the crude product obtained was subjected to column chromatography (30% MeOH-EtOAc) to provide 28 mg (84%) of the title compound. The IH NMR spectrum of this material indicated the presence of ca. 3% of the corresponding 1' R isomer. This material was dissolved in a minimum amount of methanol. Addition of diethyl ether to this solution generated 20 mg (60%) of the title compound as a crystalline white precipitate free of the 1' R isomer ($^1$H NMR). The title compound displayed the following spectral characteristics: $^1$H NMR ($CD_3D$):δ 1.60-2.00 (m, 3H), 2.25-2.43 (m, $^1$H), 5 3.59 (d of d, $^1$H, J=4.1, 12.2 Hz), 3.78 (d of d, 1H, J=31 12.2 Hz), 4.00-4.12 (m, $^1$H), 5.78 (d, 1H, J=7.4 Hz), 5.92 (d of d, $^1$H, J=31 6.7 Hz), 8.02 (d, $^1$H, J=7.5 Hz).

EXAMPLE 6

1' R- (5-FLUOROCYTOSIN-1-YL) -4' S-CARBOETHOXYTETRA-HYDROFURAN AND 1'- S- (5-FLUOROCYTOSIN-1-YL) 4'CARBOETHOXYTETRAHYDROFURAN

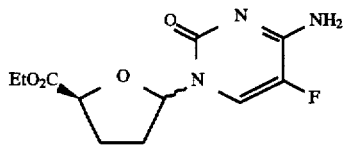

To a stirred suspension of 5-fluorocytosine (192 mg, 1.49 mmol) in dichloromethane (2 mL) containing 2,6-lutidine (346 µL, 2.98 mmol) under an argon atmosphere was added t-butyldimethylsilyl trifluoromethaziesulphonate 678 gL, 2.98 mmol). The resulting mixture was stirred for 15 minutes to give a homogeneous solution. A solution of a 2:1 mixture of 2S-carboethoxy-5R-acetoxytetrahydrofuran and 2S-carboethoxy-5S-acetoxytetrahydrofuran (250 mg, 1.24 mmol) in dichloromethane (2 mL) and iodotrimethylsilane (176 µL, 1.24 mmol) was sequentially introduced into the above solution. The reaction was allowed to proceed at room temperature for 1 hour and 30 minutes and then was quenched with a half-saturated solution of $Na_2S_2)O_3$. The resulting mixture was stirred for 5 minutes and then was transferred to a separatory funnel. The aqueous phase was removed and the organic layer was washed with saturated $Na_2S_2O_3$, water, brine and then was dried ($Na_2SO_4$). The solvent was removed under reduced pressure to provide the crude product which was subjected to column chromatography (15% MeOH-EtOAc) to afford 199 mg (59%) of the title compounds as a mixture λ7:1 (1' R,4' S):(1' S, 4' S) by $^1$H NMR). The product displayed the following spectral characteristics: $^1$H NMR (CDCl$_3$): δ 1.15–1.40 (2 overlapping t, 3H), 1.90- 2.15 (m, 2H), 2.25–2.55 (m, 2H), 4.15–4.35 (m, 2H), 4.54 (m, 0.87 Hz), 4.82 (d of d, 0.13H, J=4.4, 8.0 Hz), 5.70–6.80 (unresolved m, $^1$H), 6.09 (m, 1H), 7.40 (d, 0.13H, J=6.7 Hz), 7.90–8.60 (unresolved m, 1H), 8.48 (d, 0.87H, J=6.7 Hz).

EXAMPLE 7

1' S-(5-FLUOROCYTOSIN-1-YL)-4' R-CARBOETHOXYTETRAHYDROFURAN AND 1' R-(5-FLUOROCYTOSIN-1-YL)-4' R-CARBOETHOXYTETRAHYDROFURAN

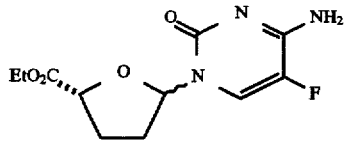

To a stirred suspension of 5-fluorocytosine (38 mg, 0.297 mmol) in dichloromethane (1 mL) containing 2,6-lutidine (69 µL, 0.594 mmol) under an argon atmosphere was added t-butyldimethylsilyl trifluoromethanesulphonate (137 µL, 0.594 mmol). The resulting mixture was stirred for 15 minutes to give a homogeneous solution. A solution of a 5:4 mixture of 2R-carboethoxy-5S-acetoxytetrahydrofuran and 2R- carboethoxy-5R-acetoxytetrahydrofuran (50 mg, 0.248 mmol) in dichloromethane (1 mL) and iodotrimethylsilane (35 µL, 0.248 mmol) was sequentially introduced into the above solution. The reaction was allowed to proceed at room temperature for 1 hour and 45 minutes and then was quenched with a half-satuirated solution of $Na_2S_2O_3$. The resulting mixture was stirred for 5 minutes and then was transferred to a separatory funnel. The aqueous phase was removed and the organic layer was washed with saturated $Na_2S_2O_3$, water, brine and then was dried ($Na_2So_4$). The solvent was removed under reduced pressure to provide the crude product which was subjected to column chromatography (15% MeOH-EtOAc) to afford 52 mg (77%) of the title compounds as a 11:2 [(1' R,4' R):(1' S,4' R)] mixture ($^1$H Ne). The product displayed the following spectral characteristics: $^1$H NMR (CDCl$_3$):δ 1.15–1.40 (2 overlapping t, 3H), 1.90-2.10 (m, 2H), 2.25–2.60 (m, 2H), 4.15–4.35 (m, 2H), 4.57 (m, 0.85 Hz), 4.84 (d of d, 0.15H, J=4.2, 7.8 Hz), 5.50–6.30 (unresolved m, 1H), 6.09 (m, IH), 7.43 (d, 0.15H, J=6.7 Hz), 7.50–9.00 (unresolved m, IH), 8.56 (d, 0.85H, J=6.7 Hz).

EXAMPLE 8

β-L-(5-FLUORO)-2' , 3$^1$-DIDEOXYCYTIDINE

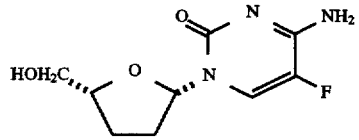

To a cold (0° C.) stirred suspension of 1' R-(5-fluorocytosin-1-yl)-4' R-carboethoxytetrahydrofuran and 1' S-(5-fluorocytosin-1-yl)-4' R-carboethoxytetrahydrofuran [307 mg, 1.133 mmol, a 4:1 (1' R,4' R):(1' S, 4' R) mixture of the isomers] in 4 mL of ethanol was added sodium borohydride (86 mg, 2 equivalents). The resultant mixture was stirred for 5 minutes and the cooling bath was removed. Stirring was continued for 75 minutes at room temperature. The reaction was quenched by the addition of 4 drops of concentrated ammonium hydroxide. After the mixture had been stirred for 15 minutes, the solvent was removed under reduced pressure and the crude product was subjected to column chromatography (25% MeOH-EtOAc) to provide 197 mg (76%) of the expected 4' -hydroxymethyl products as a 4:1 mixture. One of the fractions collected was found to contain the title compound in 97% purity (IH NMR). This fraction was concentrated to give 14 mg of a light beige coloured foam. UV ('$_{max}$): 282.7, 236.4, 206.7 nm (MeOH); [α]$_D$–81° (c, 0.7 MeOH); $^1$H NMR (CD$_3$OD): δ1.77–1.90 (m, 2H), 1.90–2.03 (m, 1H), 2.25–2.42 (m, 1H), 3.61 (d of d, 1H, J=3.3, 12.3 Hz), 3.82 (d of d, 1H, J=2.8, 12.3 Hz), 4.06 (m, 1H), 5.87 (m, 1H), 8.32 (d, 1H, J=7.0 Hz).

EXAMPLE 9

β-D-(5-FLUORO)-2' -3' -DIDEOXYCYTIDINE

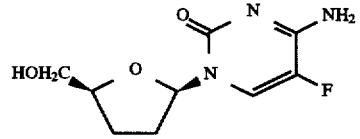

To a cold (0° C.) stirred suspension of 1$^1$R-(5-fluorocytosin-1-yl)-4 ' S-carboethoxytetrahydrofuran and 1' S-(5-fliuorocytosin-1-yl)-4' S-carboethoxytetrahydrofuran

[199 mg, 0.734 mmol, a 7:1 (1' R,4' S):(1' S, 4' S) mixture of the isomers] in 3 mL of ethanol was added sodium borohydride (56 mg, 2 equivalents). The resultant mixture was stirred for 5 minutes and the cooling bath was removed. Stirring was continued overnight (ca. 16 hours) at room temperature. The reaction was quenched by the addition of 4 drops of concentrated ammonium hydroxide. After the mixture has been stirred for 15 minutes, the solvent was removed under reduced pressure and the crude product was subjected to column chromatography (20% MEOH-EtOAc) to provide 112 mg (67%) of the expected 4'-hydroxymethyl products as a 7:1 (1' R,4' S):(1' S,4' S) mixture ($^1$H NMR). One of the fractions collected was found to contain the title compound only (H NMR). This fraction was concentrated in vacuo to give 27 mg of a white foam; UV (λmax): 283.6,, 238.2, 202.4 nm (MeOH); $[\alpha]_D^{96°}$ (c, 0.7 MeOH); $^1$H NMR (CD$_3$OD): δ 1.77–1.90 (m, 2H), 1.90–2.03 (m, $^1$H), 2.25–2.42 (m, $^1$H), 3.61 (d of d, 1H, J=3.3, 12.3 Hz), 3.82 (d of d, 1H, J=2.8, 12.3 Hz), 4.06 (m, 1H), 5.87 (m, 1H), 8.32 (d, 1H, J=7.0 Hz).

While we have presented a number of embodiments of our invention, many alternatives, modifications and variations of these embodiments will be apparent to those of ordinary skill in the art. Therefore, it will be appreciated that: the scope of this invention is to be defined by the following claims, rather than the specific examples presented above.

We claim:

1. A diastereoselective process for producing optically active cis-nucleosides and nucleoside analogues and derivatives of formula (I)

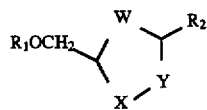

wherein

R$_1$ is hydrogen or acyl;

R$_2$ is a desired purine or pyrimidine base or an analogue or derivative thereof;

W is S, S=O, or SO$_2$O, NZ, or CH$_2$;

X is O, S, S=O, or So$_2$O,NZ, CH$_2$, CHF, CH, CHN$_3$, or CHOH;

Y is O, S, CH$_2$, CH, CHF, or CHOH; and

Z is hydrogen, hydroxyl, alkyl or acyl;

provided that W is not O, S, S=O or SO$_2$ when Y is CH$_2$ and X is O, S, S=O or S$_2$;

the process comprising the step of glycosylating the desired purine or pyrimidine base or analogue or derivative thereof with a single enantiomer of the compound of formula (II)

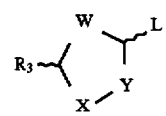

wherein

R3 is a substituted carbonyl or carbonyl derivative; and

L is a leaving group, using a Lewis: acid of the formula (III)

wherein

R$_5$, R$_6$ and R$_7$ are independently selected from the group consisting of hydrogen; C$_{1-20}$ alkyl optionally substituted by fluoro, bromo, chloro, iodo, C$_{1-6}$ alkoxy or C$_{6-20}$ aryloxy; C$_{7-20}$ aralkyl optionally substituted by halogen, C$_{1-20}$ alkyl or C$_{1-20}$ alkoxy; C$_{6-20}$ aryl optionally substituted by fluoro, bromo, chloro, iodo, C$_{1-20}$ alkyl or C$_{1-20}$ alkoxy; trialkylsilyl; fluoro; bromo; chloro and iodo; and R$_8$ is selected from the group consisting of fluoro; bromo; chloro; iodo; C$_{1-20}$ sulphonate esters, optionally substituted by fluoro, bromo, chloro or iodo; C$_{1-20}$ alkyl esters optionally substituted by fluoro, bromo, chloro or iodo; polyvalent halides; trisubstituted silyl groups of the general formula (R$_5$) (R$_6$) (R$_7$)Si (wherein R$_5$, R$_6$, and R$_7$ are as defined above); saturated or unsaturated selenenyl C$_{6-20}$ aryl; substituted or unsubstituted C$_{6-20}$ arylsulfenyl; substituted or unsubstituted C$_{6-20}$ alkoxyalkyl; and trialkylsiloxy.

2. The process according to claim 1, further comprising the step of reducing R$_3$ of the glycosylated purine or pyrimidine base or analogue or derivitive therof to produce the optically active cis-nucleoside or nucleoside analogue or derivative of formula (I).

3. The process according to claim 1, further comprising the step of resolving the compound of formula (II) into a single enantiomer using a chiral auxiliary before glycosylating the desired purine or pyrimidine base.

4. The process according to claim 3, wherein the chiral auxiliary is selected from the group consisting of:

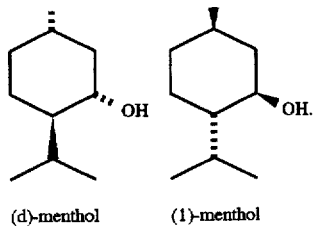

(d)-menthol    (1)-menthol

5. The process according to any one of claims 1 to 3, wherein R$_2$ is a pyrimidine base.

6. The process according to claim 5, wherein the pyrimidine base is 5-fluorocytosine.

7. The process according to claim 5, wherein the pyrimidine base is cytosine.

8. The process according to any one of claims 1 to 3, wherein the Lewis acid is selected from the group consisting of trimethylsilyl triflate and iodotrimethylsilane.

9. The process according to any one of claim 1 to 3, wherein R$_3$ is selected from the group consisting of —C(O) —OR, wherein R is an alkyl group; —COOH; —C(O)—N (Et)$_2$; —C(O)CH$_3$; —C(O)—Ph and

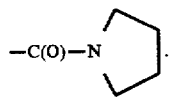

10. The process according to claim 9, wherein the R$_3$ is selected from the group consisting of —C(O)OR, wherein R is an alkyl group, and —C(O)OH.

* * * * *